(12) United States Patent
Hamamatsu et al.

(10) Patent No.: US 7,332,359 B2
(45) Date of Patent: Feb. 19, 2008

(54) SEMICONDUCTOR DEVICE INSPECTION METHOD

(75) Inventors: Akira Hamamatsu, Yokohama (JP);
Minori Noguchi, Mitsukaido (JP);
Yoshimasa Ohshima, Yokohama (JP);
Hidetoshi Nishiyama, Fujisawa (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 10/082,593

(22) Filed: Feb. 22, 2002

(65) Prior Publication Data

US 2003/0022401 A1 Jan. 30, 2003

(30) Foreign Application Priority Data

Jul. 24, 2001 (JP) ............................. 2001-222405

(51) Int. Cl.
*H01L 31/26* (2006.01)
(52) U.S. Cl. .................. 438/14; 438/16; 257/E21.521; 356/239.1; 702/84; 702/109
(58) Field of Classification Search .................. 438/14, 438/16, 10, 15, 12, 11, 17, 18; 356/237, 356/239.1, 239.8; 702/81, 84, 109; 703/13, 703/19, 20, 23; 382/144; 257/E21.521, 257/E21.531
See application file for complete search history.

(56) References Cited

U.S. PATENT DOCUMENTS

| | | | | |
|---|---|---|---|---|
| 6,115,546 A | * | 9/2000 | Chevallier et al. | 716/5 |
| 6,374,199 B1 | * | 4/2002 | Sugimoto | 703/2 |
| 6,444,382 B1 | * | 9/2002 | Sarig et al. | 430/30 |
| 6,458,610 B1 | * | 10/2002 | Lensing et al. | 438/16 |
| 6,470,489 B1 | * | 10/2002 | Chang et al. | 716/21 |
| 6,483,938 B1 | * | 11/2002 | Hennessey et al. | 382/149 |
| 6,549,863 B1 | * | 4/2003 | Morinaga | 702/81 |
| 6,553,329 B2 | * | 4/2003 | Balachandran | 702/118 |
| 6,578,188 B1 | * | 6/2003 | Pang et al. | 716/19 |
| 6,603,873 B1 | * | 8/2003 | Gordon et al. | 382/144 |
| 6,757,645 B2 | * | 6/2004 | Chang et al. | 703/13 |
| 6,771,806 B1 | * | 8/2004 | Satya et al. | 382/149 |

* cited by examiner

*Primary Examiner*—Wai-Sing Louie
*Assistant Examiner*—(Vikki) Hoa B Trinh
(74) *Attorney, Agent, or Firm*—Townsend and Townsend and Crew LLP (57) ABSTRACT

Techniques for inspecting semiconductor devices. An inspection condition using chip matrix data and chip size data is set. The intricate circuit patterns of at least one semiconductor device is inspected with the inspection condition. In an embodiment of the present invention, inspection uses images formed by the irradiation of white light, a laser light, or an electron beam. Data obtained from the inspection is used to generate a revised inspection condition. Semiconductor devices are inspected using the revised inspection condition.

10 Claims, 13 Drawing Sheets

FIG.1 SETTING INSPECTION CONDITIONS (PRIOR ART)

FIG.3

SETTING CHIP SIZE

FIG.4

SETTING SHOT MATRIX

SHOT COMPARISON    CHIP COMPARISON    CELL COMPARISON

SET THE COMPARISON METHOD TO SUIT THE REPETITIVE UNIT

SETTING THE INSPECTION SEQUENCE

FIG.6

SETTING CHIPS TO BE EXCLUDED
FROM INSPECTION

FIG.7

☐ AREAS TO BE INSPECTED

▨ AREAS EXCLUDED FROM INSPECTION (SCRIBE AREA)

SETTING AREAS TO BE INSPECTED
AND AREAS TO BE EXCLUDED

FIG.8

SELECT PATTERNS AND MATERIAL
THAT WILL MAKE IMAGES EASILY
RECOGNIZABLE DURING ALIGNMENT

SETTING THE
ALIGNMENT PATTERN

FATALITY JUDGEMENT
(BY PRODUCT, PROCESS, AND AREA)

FIG.11

AUTOMATIC DEFECT CLASSIFICATION
TECHNOLOGY

FIG.12

(A) CORRESPONDING POINT (B) FREQUENCY — SIGNAL VALUE HISTOGRAM — NORMAL PART, THRESHOLD VALUE, ABNORMAL PART (UNDETECTED)

FIG.13

(A) CORRESPONDING AREAS (PARAMETER ADDITION)

(B) FREQUENCY — SIGNAL VALUE HISTOGRAM — NORMAL PART, THRESHOLD VALUE, ABNORMAL PART (DETECTED)

FIG.14

ESTIMATE THE SIGNAL INTENSITY FROM PATTERN
PITCH AND CONTROL THE AMOUNT OF LIGHT

SETTING THE AMOUNT OF LIGHT

FIG.15

SETTING AREAS IN WHICH
MANY FALSE ALARMS OCCUR

AREAS IN WHICH MANY
FALSE ALARMS OCCUR ( SCRIBE AREA
AROUND MEMORY MAT )

SEMICONDUCTOR DEVICE INSPECTION METHOD

BACKGROUND OF THE INVENTION

1. Field of the Invention

The present invention relates to a method for inspecting semiconductor devices, liquid crystals, and magnetic heads.

An example in which a semiconductor wafer is inspected will be explained.

2. Description of the Related Art

Semiconductor devices are manufactured by repeating a process that uses lithography or etching to transfer a pattern, usually formed on a photomask, onto a semiconductor wafer. In a semiconductor device manufacturing process, the quality of the lithography or etching, the quality of various other types of processing, and the production of foreign matter can greatly affect the semiconductor device yield. Therefore, methods for inspecting semiconductor wafers from a manufacturing process have conventionally been implemented to detect anomalies or faults early or before they occur.

Methods for inspecting for defects in patterns on semiconductor wafers involve the use of a defect inspection device that irradiates the semiconductor wafer with white light and uses the optical image to compare the same circuit patterns on a plurality of LSI. For example, as disclosed in Japanese Patent Laid-open H3-167456, in an inspection method that uses optical images, the optically illuminated area on a substrate is imaged on an integrated time delay sensor. Defects are detected by comparing the image detected by the sensor and design information already entered.

In the aforementioned defect inspection, adjoining identical circuit pattern images are formed. These images are then compared and defects automatically detected. However, inspections must also handle wafers that have various pattern layouts or patterns that involve various materials. To accurately compare adjoining patterns, the positioning of the pattern, that is the chip (die) and shot matrices on the wafer, must be predetermined and preset as inspection conditions for wafers to be inspected. In addition, to enable the formation of images suitable for inspection in various materials, appropriate values must be set for image brightness and the pattern-substrate contrast and these values preset as inspection conditions for wafers to be inspected. However, there are no descriptions of the procedures or operation methods for these inspection condition settings for the above conventional devices and their operation is complex, between one and several hours being required to set appropriate inspection conditions for a new wafer to be inspected. A problem exists in that, in order to implement pattern inspections for a plurality of products (that is a plurality of circuit pattern matrices) and a plurality of processes (that is a plurality of materials and a plurality of detailed circuit pattern forms) in a semiconductor manufacturing line, a huge number of inspection conditions must be set. As a result, an enormous amount of time is required in all inspection operations and in particular, in inspection condition setting operations.

Japanese Patent Laid-open 2001-35893 discloses a method for improving operation efficiency when the above inspection conditions are set and for reducing the time involved in setting inspection conditions. The design of the operation screen layout reduces the time needed for the entry of setting items but even so, between thirty minutes and several hours are required to set inspection conditions in the inspection device.

Figure 1:
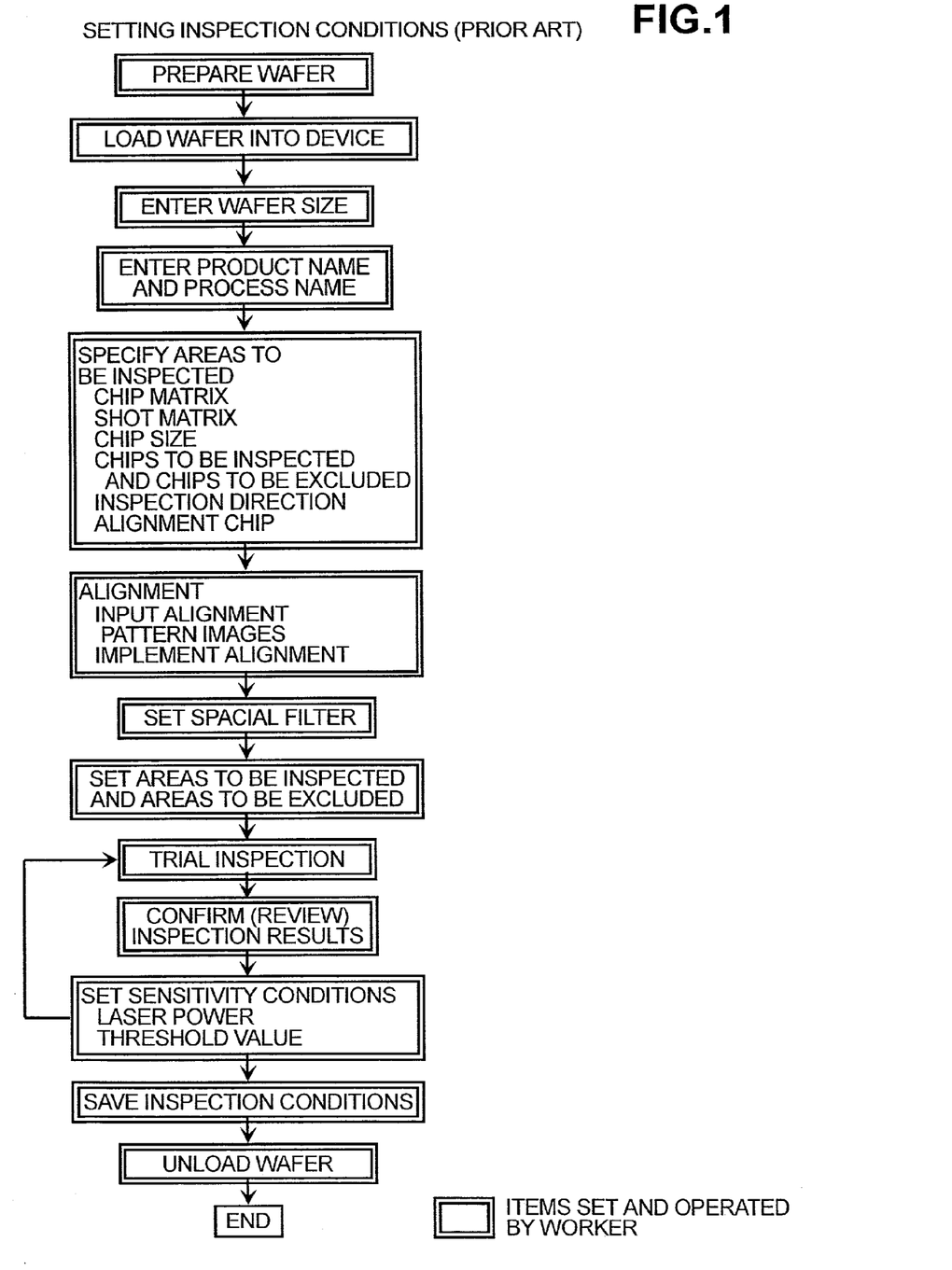
FIG. 1 is a flowchart showing the sequence involved in setting inspection conditions according to conventional technology.

FIG. 1 is one conventional example of inspection condition settings and shows a conditions setting sequence for a foreign matter inspection device that uses scattered laser light. The conventional setting of inspection conditions starts with preparation of a wafer and loading of that wafer into the device. As preliminary preparation for inspection, the chip matrix within the wafer, the shot matrix when the pattern is exposed, the chip size, and test element group (TEG) chips for process and yield management must be set so that they will not be inspected and the direction of the wafer scan during the inspection and the chips to be used in alignment must be set. Furthermore, a pattern that uses automatic alignment is selected, the image data of the alignment pattern saved, and actual alignment implemented.

After the above settings are completed, adjustment of the inspection sensitivity starts. Firstly, an special filter that efficiently shields diffracted light from repetitive patterns on the chip is set. A trial inspection then takes place. The detection results are confirmed (reviewed) after the trial inspection and a temporary laser power value and threshold value, which are sensitivity conditions, are set. After repeating the sensitivity condition settings, trial ion and review, and then determining inspection conditions so that less than a certain percentage of false alarms occur, the inspection conditions are saved and the wafer unloaded. This ends the extraction of conditions.

In a device that inspects various types of intricate patterns including those on semiconductor devices as in the above description of conventional technology, various inspection conditions must be set and these conditions must be adjusted for each product and each process. The inspection device is occupied while conditions are being extracted, thus actually reducing inspection time. Also, because there are a plurality of entry items, a worker who sets conditions requires a certain amount of training and must be experienced in the use of the device. Furthermore, while conditions are being extracted, there is an accumulation of semiconductor products. Therefore, the turnaround time (TAT) of semiconductor devices is extended and costs increase.

SUMMARY OF THE INVENTION

The present invention provides a technology for inspecting intricate circuit patterns that uses images formed by irradiating white light, laser light, or an electron beam, and that minimizes user input by using semiconductor device design data when setting the various conditions required for inspection.

By using semiconductor device design data, the present invention also provides a technology that temporarily determines the above inspection condition settings before semiconductor devices requiring inspection reach the inspection process. This minimizes the time taken to set inspection conditions.

By using semiconductor device design data, the present invention further provides a technology that produces inspection results, the number of false alarms caused by the highly sensitive inspection that occur during defect detection being held below a certain percentage thereof.

By using semiconductor device design data, the present invention further provides a technology that judges whether or not detected defects are in areas wherein false alarms are likely to occur, and that, in the setting of inspection conditions, gives priority to the review of defects in areas in which false alarms tend to occur by adding that judgement information to inspection results.

By using semiconductor device design data, the present invention further provides a technology that enables inspection sensitivity to be set to any level to suit the design rules for each area within a semiconductor device chip or to suit the degree of functional importance.

By using semiconductor device design data, the present invention further provides a technology that determines whether defects are in a transparent film or non-transparent film, that adds this information to the detected defect results, and that distinguishes between defects that can and cannot be confirmed using a scanning electron microscope (SEM).

By using semiconductor device design data, the present invention further provides a technology that, in the classification of detected defects, determines if the defect is in a specific pattern or specific material and that obtains information that is useful in defect classification.

In short, according to the present invention, a semiconductor device inspection device is equipped with a function that, through the use of semiconductor device design data, enables a plurality of parameters to be automatically set.

The present invention is also equipped with a function that, through the use of semiconductor device design data, increases the number of detection signal parameters from specific repetitive patterns used in statistical processing during defect detection.

According to the present invention, a semiconductor device inspection device is further equipped with a function that, through the use of semiconductor device design data, adds, to detection results, information as to whether or not the area in which a defect was detected is one in which false alarms tend to occur. The present invention is also equipped with a function that, based on this supplementary information, can isolate and review those defects in areas in which false alarms tend to occur.

The present invention is further equipped with a function that, through use of the semiconductor device design data, determines if the defect is in a transparent film or non-transparent film and that adds this information to the defect detection results.

Also, to achieve the above objects according to the present invention, the semiconductor device inspection method is configured to set inspection conditions using semiconductor device design data, to inspect semiconductor devices using these set conditions, to then use the results of inspections to revise inspection conditions set using design data, and to inspect semiconductor devices using these revised inspection conditions.

Also, in the present invention, the semiconductor device inspection method is configured to extract related information from a design data base that specifies the product names of semiconductor devices and the names of processes used to process them, that sets inspection conditions using this extracted related information, that inspects semiconductor devices using these set conditions, that than uses the results of inspections to revise set inspection conditions using design data, and that then inspects semiconductor devices using these revised inspection conditions.

These and other objects, features and advantages of the invention will be apparent from the following more particular description of preferred embodiments of the invention, as illustrated in the accompanying drawings.

DESCRIPTION OF THE PREFERRED EMBODIMENTS

Figure 2:
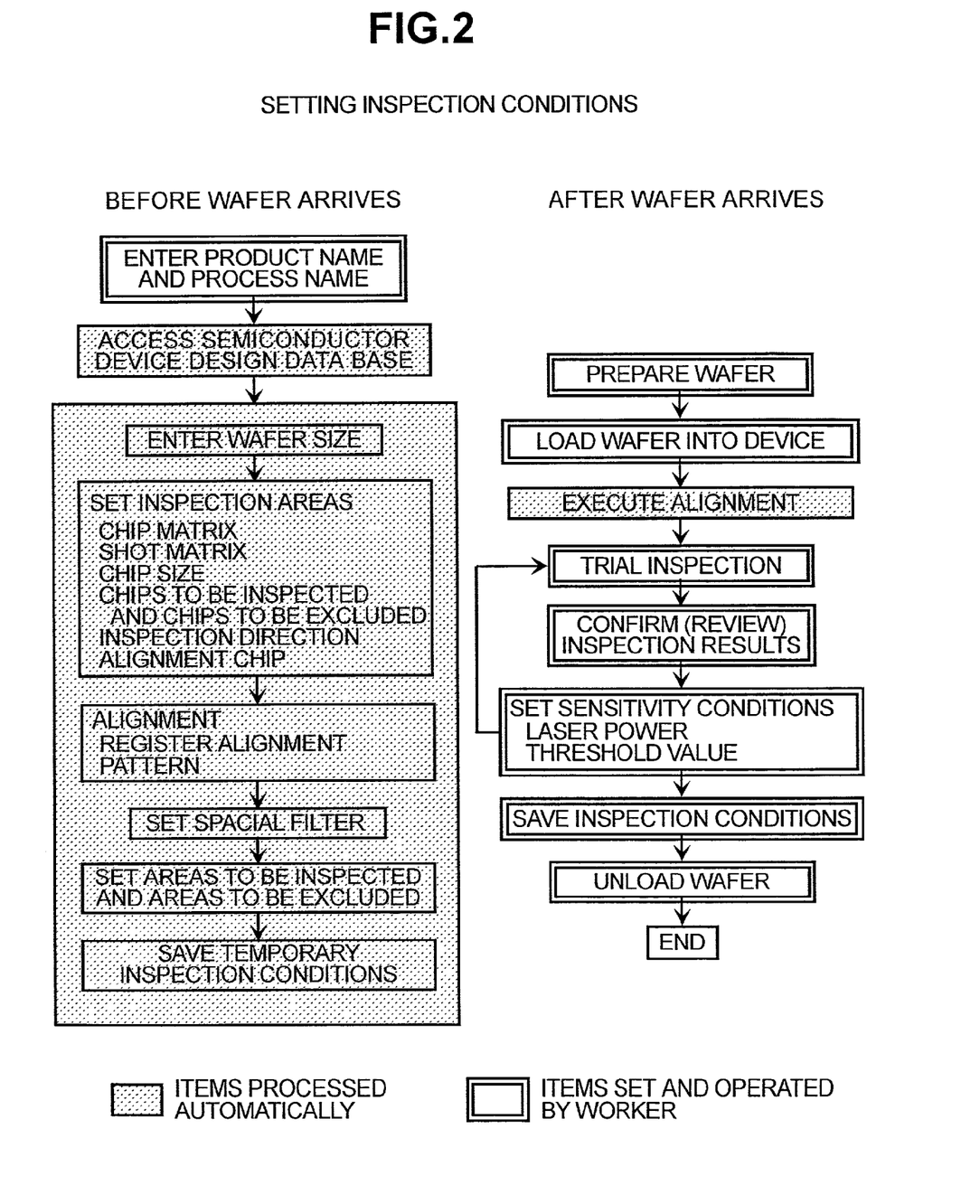
FIG. 2 is a flowchart showing the sequence involved in setting inspection conditions according to the present invention.

FIG. 2 shows an example of a sequence relating to the setting of inspection conditions according to the present invention. Firstly, inspection conditions are temporarily determined prior to the wafer actually arriving at the inspection process. This enables minimization of wafer accumulation time while conditions are being set.

Firstly, the product name of the semiconductor device to be inspected and the name of the process in which the semiconductor device is processed immediately prior to inspection are entered from a terminal. When the product name and process name are entered, the semiconductor device design data base is accessed via a communication means and the data required for inspection preliminary preparation collected. The conditions required for inspection are then automatically set in the steps sown in FIG. 2. A worker can enter the product name and process name settings by any means such as a keyboard or a barcode reader. Entries can be made from within a clean room, or from a personal computer outside a clean room that can access the device.

This ends the preliminary preparation for the setting of conditions in an inspection device.

Since there are only two entries to be made, that is, the product name and process name, the worker need not be skilled in the use of the inspection device.

Next, the setting of sensitivity levels after the wafer has actually arrived will be explained.

Alignment automatically starts when the wafer is loaded into the device. After alignment has ended, sensitivity condition settings (laser power, threshold value), a trial inspection, and a review are repeated. Then, after inspection conditions that enable only actual reviewed and classified defects to be detected and inspection conditions that enable false alarms to be held below a certain percentage are determined, these conditions are saved and the wafer unloaded. This ends the extraction of conditions. These saved inspection conditions and images of reviewed defects can be confirmed on the screen.

After inspection conditions are thus determined, wafers processed in the previous process are sequentially inspected using these determined inspection conditions. Wafers that have been inspected are sent to the next process and processed in that next process. The results of the inspections are displayed on screen and stored in a storage means.

The time involved in work within the conditions setting sequence, other than "sensitivity condition settings", "trial inspection" and "review", will take between several seconds and several tens of seconds.

The time involved in "sensitivity condition settings", "trial inspection" and "review" can be greatly reduced through the use of an automatic defect review (ADR) function and an automatic defect classification (ADC) function. The time required for setting conditions can be greatly reduced to between several minutes and several tens of minutes.

Items that are automatically set after the semiconductor device design data base is accessed in preparation for inspection device condition settings will be explained below.

Figure 3:
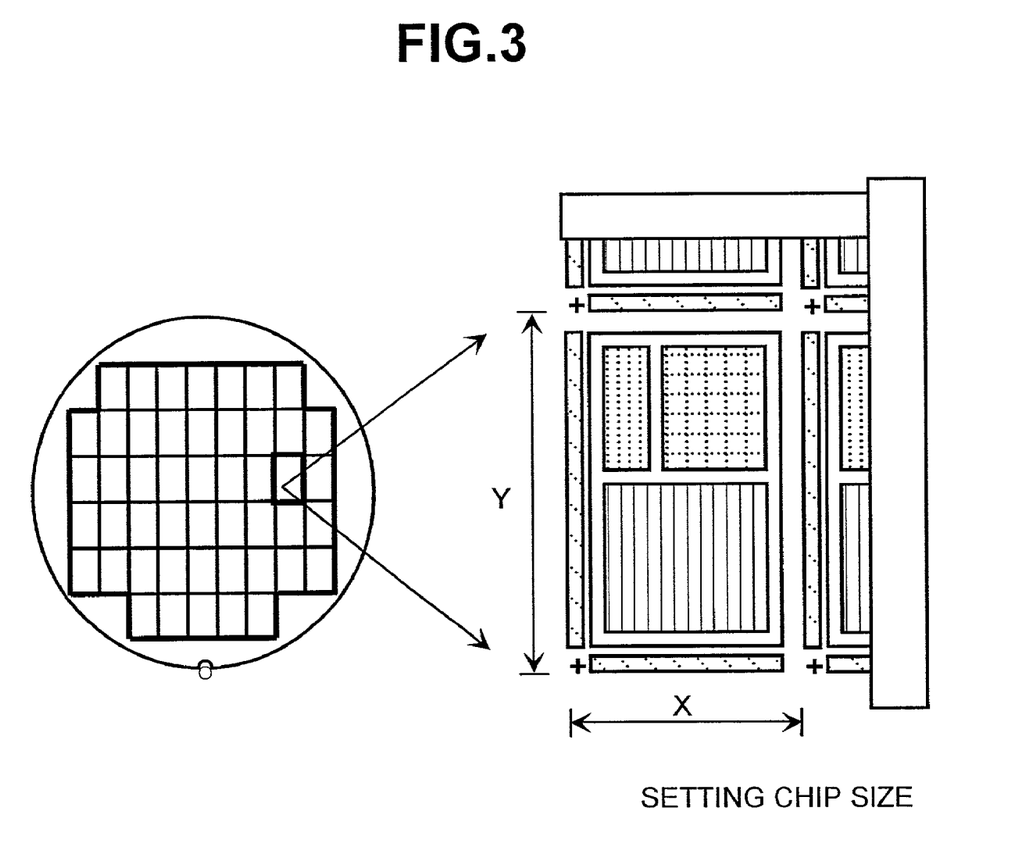
FIG. 3 is a plan view of a wafer and chip used in the explanation of chip matrix and chip size settings.

FIG. 3 shows settings for a chip matrix and for chip size. There are places on a wafer on which there is no chip pattern and during inspection these chips will not be inspected. For example, touching of the wafer periphery by sane parts of chips very close to the periphery of the wafer and film thickness irregularities can cause the semiconductor device to not work. These chips are removed as targets of inspection by automatically deleting them. In a chip size setting, the size in the x-direction of the chip and the size in the y-direction are set.

Figure 4:
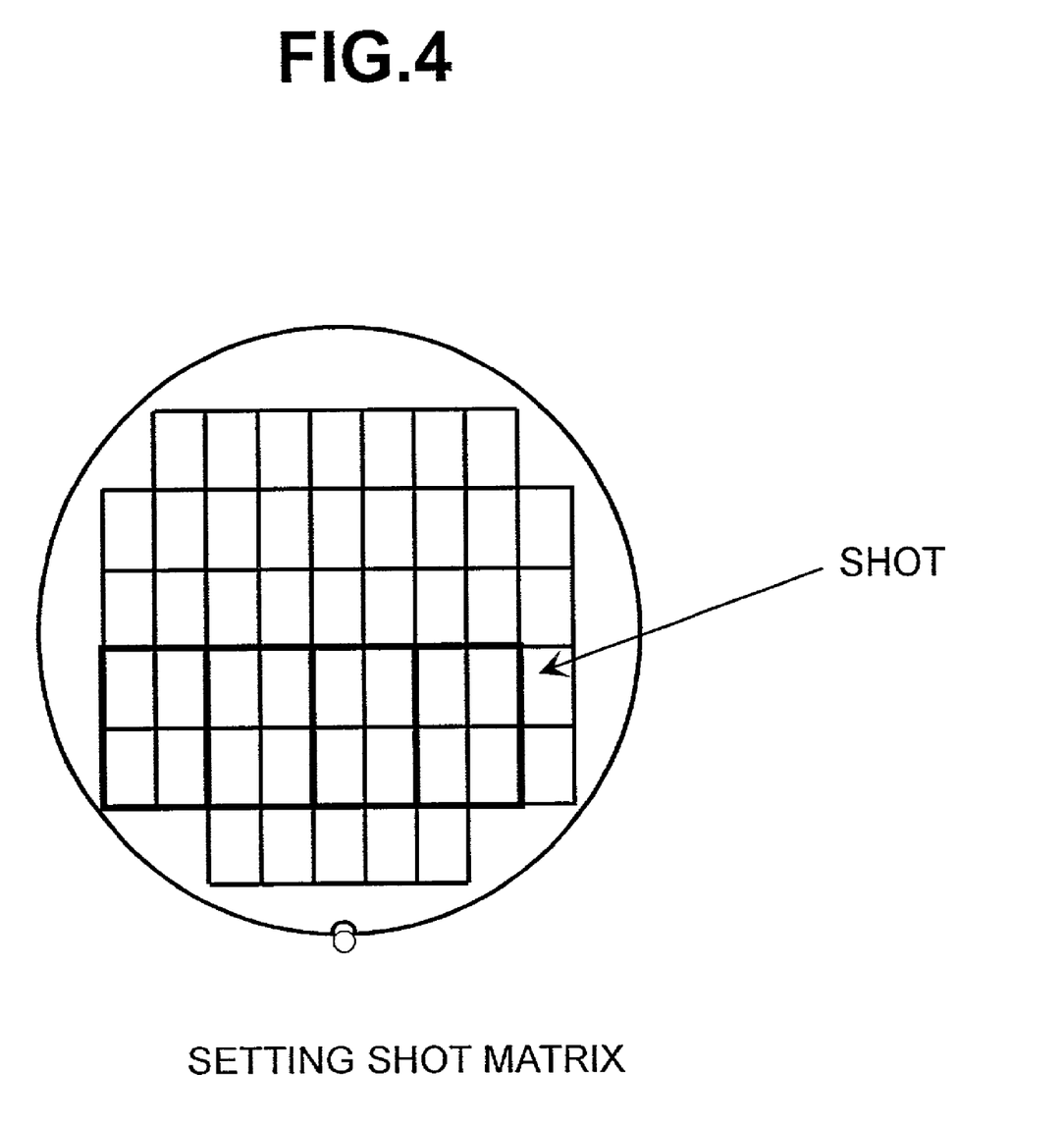
FIG. 4 is a plan view of a wafer used in the explanation of a shot matrix.

FIG. 4 shows settings for a shot matrix. When a semiconductor device pattern is exposed, a plurality of chips are sometimes exposed together. In that case, different (same for shot unit) patterns are formed for each chip on the periphery (scribe area) of the chips. Here, when ordinary chips undergo a comparison inspection, a false alarm will sound for the scribe area and the section sequence in the scribe area will therefore have to be changed.

Figure 5:
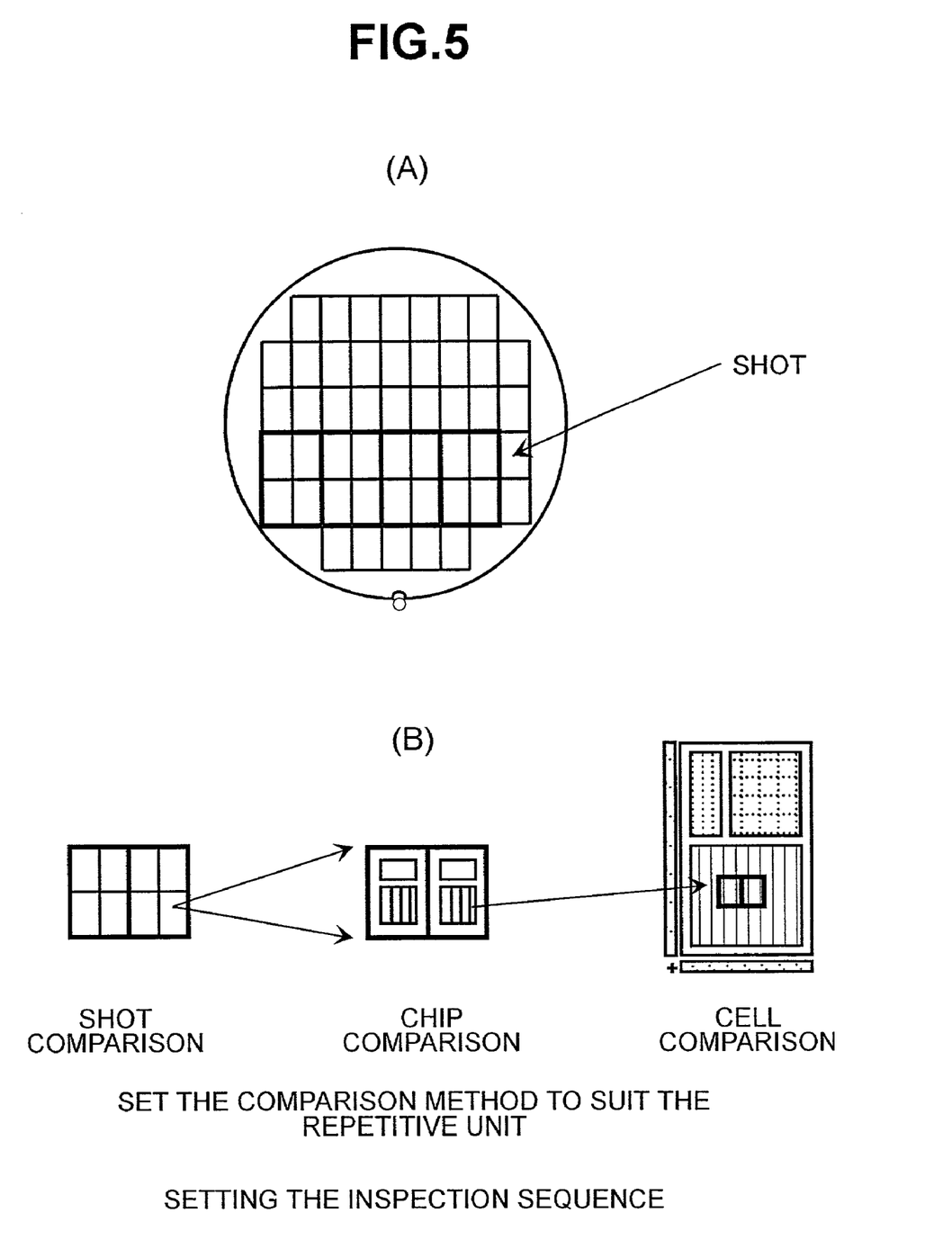
FIG. 5(a) is a plan view of a wafer used in the explanation of inspection sequence settings.
FIG. 5(b) is a plan view of a chip used in the explanation of inspection sequence settings.

FIG. 5(a) shows a shot area on a wafer and FIG. 5(b) shows a diagram of a chip that will be used to explain the inspection sequence and shows how a comparison method is set to suit repetitive units. That is, patterns that are repeated in shot units, such as in the scribe area, are inspected using comparison inspection in shot units. Patterns that are repeated in chip units are inspected using comparison inspection in chip units, and cell patterns such as in DRAM, SRAM, and FLASH memory are inspected using cell comparison. Because there are minor variations in the size and film thickness of the wafer surface, usually, the smaller the comparison range the lesser the variations, and inspection sensitivity is improved.

Figure 6:
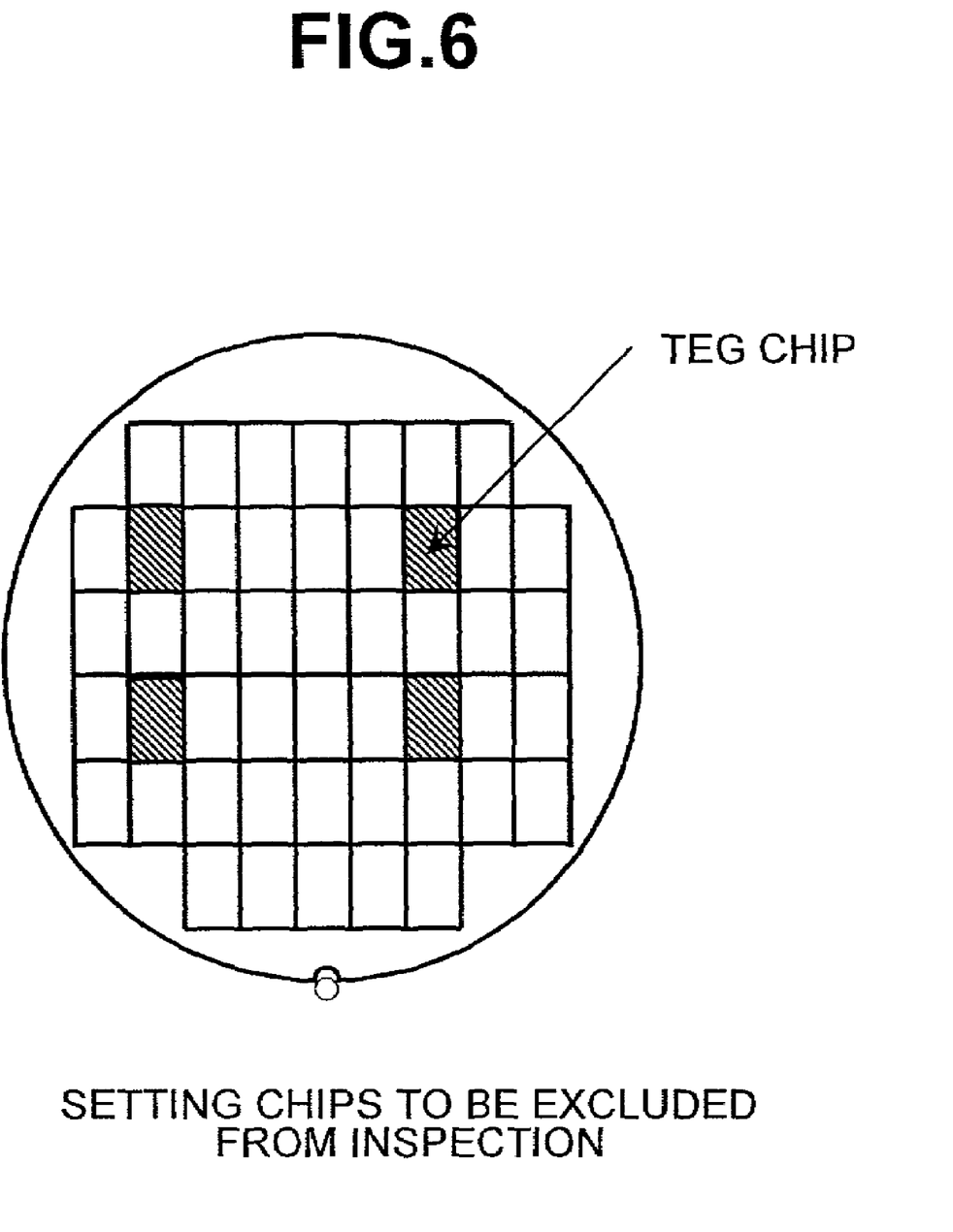
FIG. 6 is a plan view of a wafer used in the explanation of settings for chips that will and that will not be inspected.

FIG. 6 shows an example of settings for chips that will and that will not be inspected. Sometimes a wafer includes test element group (TEG) chips for managing processes and yield. These TEG chips frequently have a circuit pattern that is completely different to that of other chips and so when such dips are inspected, false alarms often occur for the TEG chip. Therefore, TEG chips are usually set so that they will not be inspected.

Figure 7:
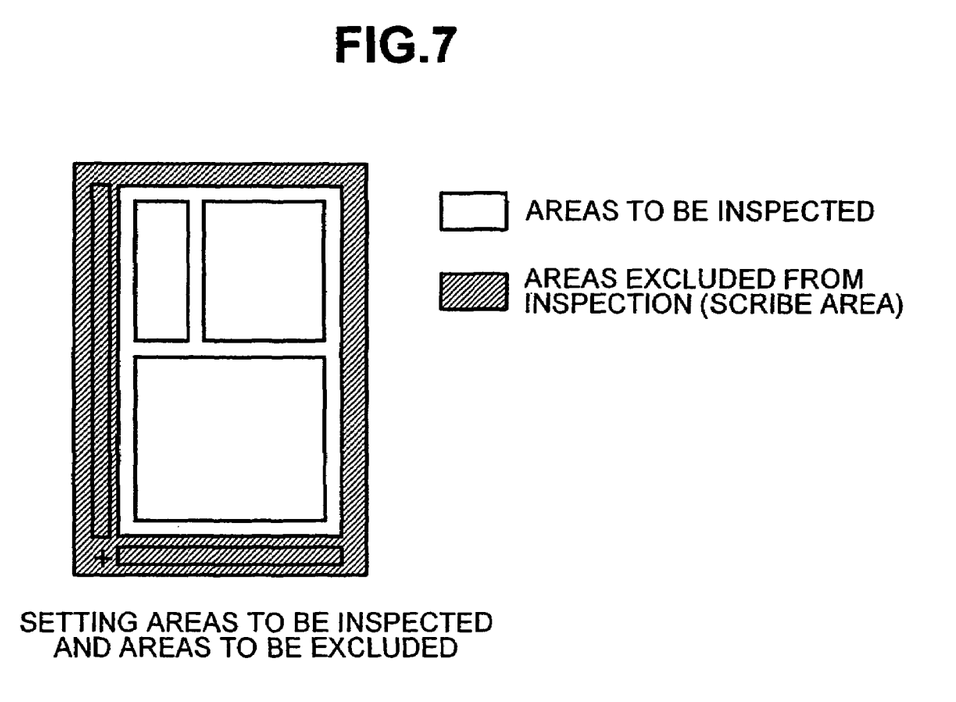
FIG. 7 is a plan view of a chip used in the explanation of settings for chips that will and that will not be inspected.

FIG. 7 shows an example in which areas that will and will not be inspected are set for a chip pattern. In this example, the scribe area is set so that it will not be inspected. This area is cut off when the chip is cut out of the wafer and so it has almost no effect on the operation of a semiconductor device. Therefore, depending on the semiconductor device manufacturer, defects in this area are sometimes excluded from management. Same particular areas, for example the yield of a cache memory area in a CPU product, affect product quality and price, and therefore when settings are being made for areas that will or will not be inspected, it is possible to set only those areas for inspection.

Figure 8:
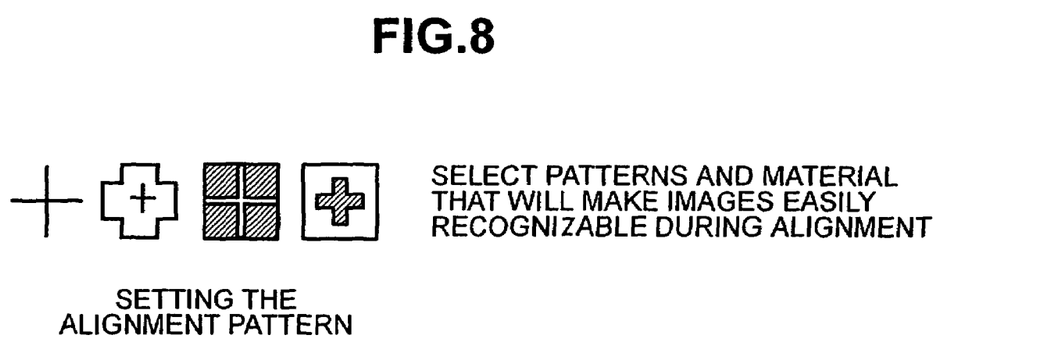
FIG. 8 is a plan view of an alignment pattern.

FIG. 8 shows the settings of an alignment pattern. In alignment, pre-registered patterns and wafer patterns that are targeted for inspection are compared beforehand and these patterns are matched. Therefore, by obtaining form information from design data, the need to capture and save images especially using an actual wafer when setting conditions is eliminated. Also, by using pattern material information, patterns with high contrasts can be set automatically.

FIG. 9(a) shows a chip and an enlarged diagram of a repetitive pattern area on the chip. FIG. 9(b) shows the signal acquisition site on a chip, FIG. 9(c) shows a detection signal acquired from this signal acquisition site prior to spacial filter settings, and FIG. 9(d) shows an example of the spacial filter settings made after a detection signal is acquired from this signal acquisition site. When light shines on a repetitive pattern in a semiconductor product, diffraction of light occurs in accordance with the pitch of the repetitive pattern and the wavelength of the light. By shielding this diffracted light, the spacial filter improves the S/N of the pattern and foreign matter and defects.

Figure 9:
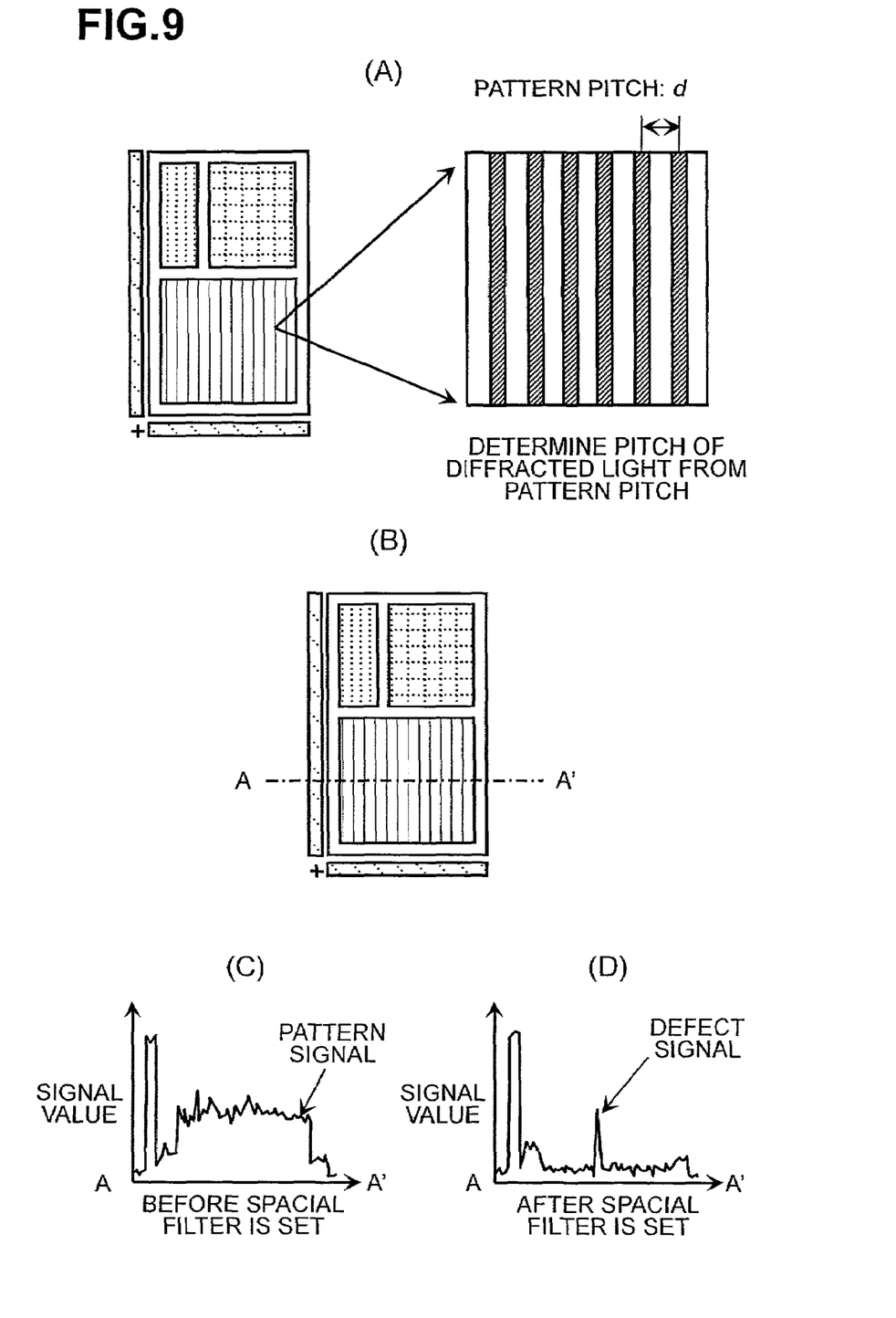
FIG. 9(a) is a plan view of a chip.
FIG. 9(b) is a plan view of a chip showing the site of signal acquisition.
FIG. 9(c) is a graph showing signal values before spacial filter settings.
FIG. 9(d) is a graph showing signal values after spacial filter settings.

Because the wavelength of the ligating is already known in the inspection device, the pattern of diffracted light can be determined by obtaining the repetitive pattern pitch size from design data. This enables automatic setting of the spacial filter. The bottom section of FIG. 9 shows a comparison before and after the spacial filter settings are made, and thus shows an example of how the pattern signals are lower when the special filter is set and how defects that were previously hidden within the pattern signal can now be detected. Spacial filters can also be set for each inspection area. In this case, the noise from patterns in each area can be suppressed to enable highly sensitive detection.

Figure 10:
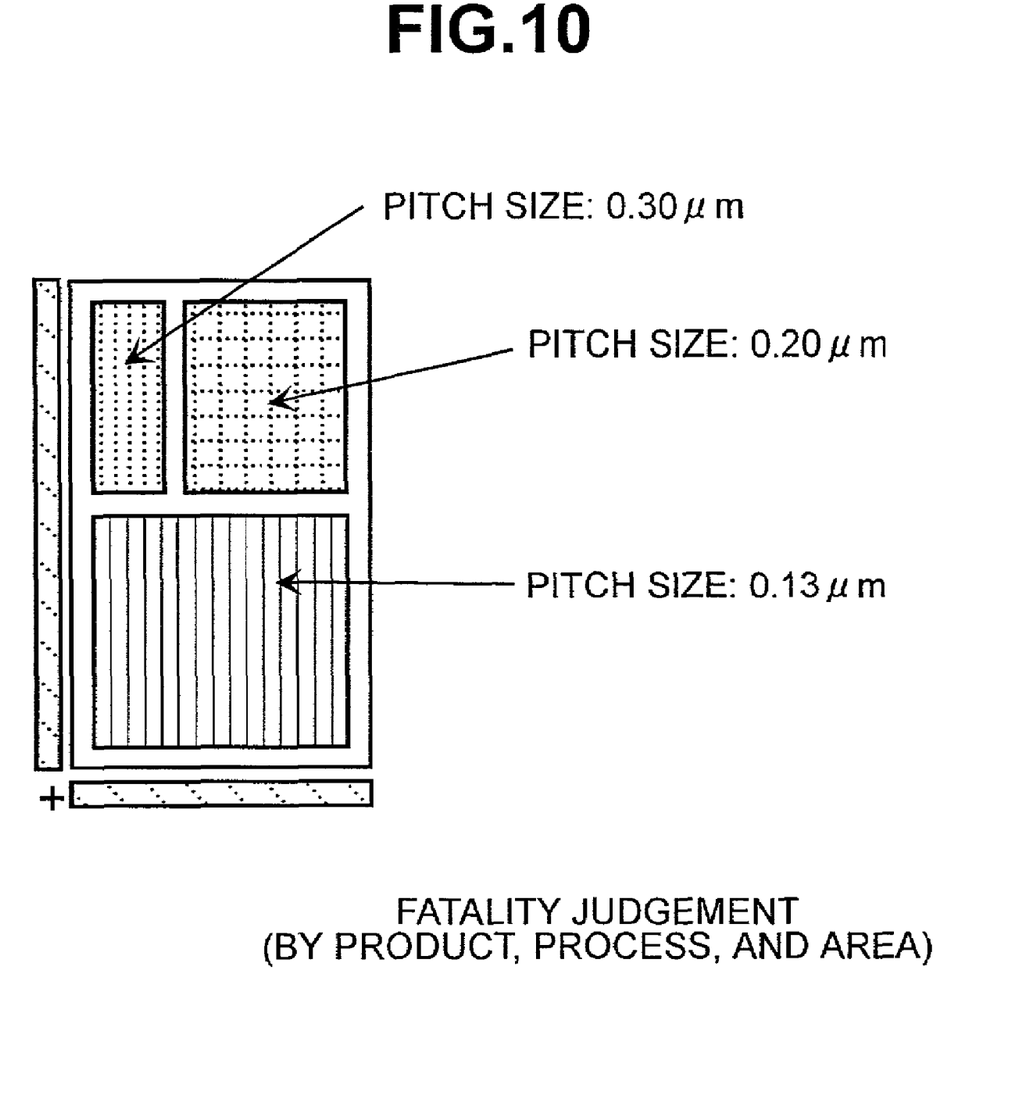
FIG. 10 is a plan view of a chip.

FIG. 10 shows an example in which sensitivity is set for each inspection area. For example, even if there is a 0.1 mm piece of foreign matter in a wiring portion of 0.5 mm pitch, this foreign matter will have almost no effect on yield. That is, too highly sensitive an inspection of this area will result in defects that have no effect on yield, that is defects that do not need to be addressed, being detected, creating a lot of noise for the person at the workplace managing the process. Therefore, by obtaining wiring rules from semiconductor device design data for each area, each area can be inspected with the sensitivity required for that area. Also, the number of the false alarms can be reduced by lowering sensitivity in those areas where false alarms often occur, for example the scribe area.

Figure 11:
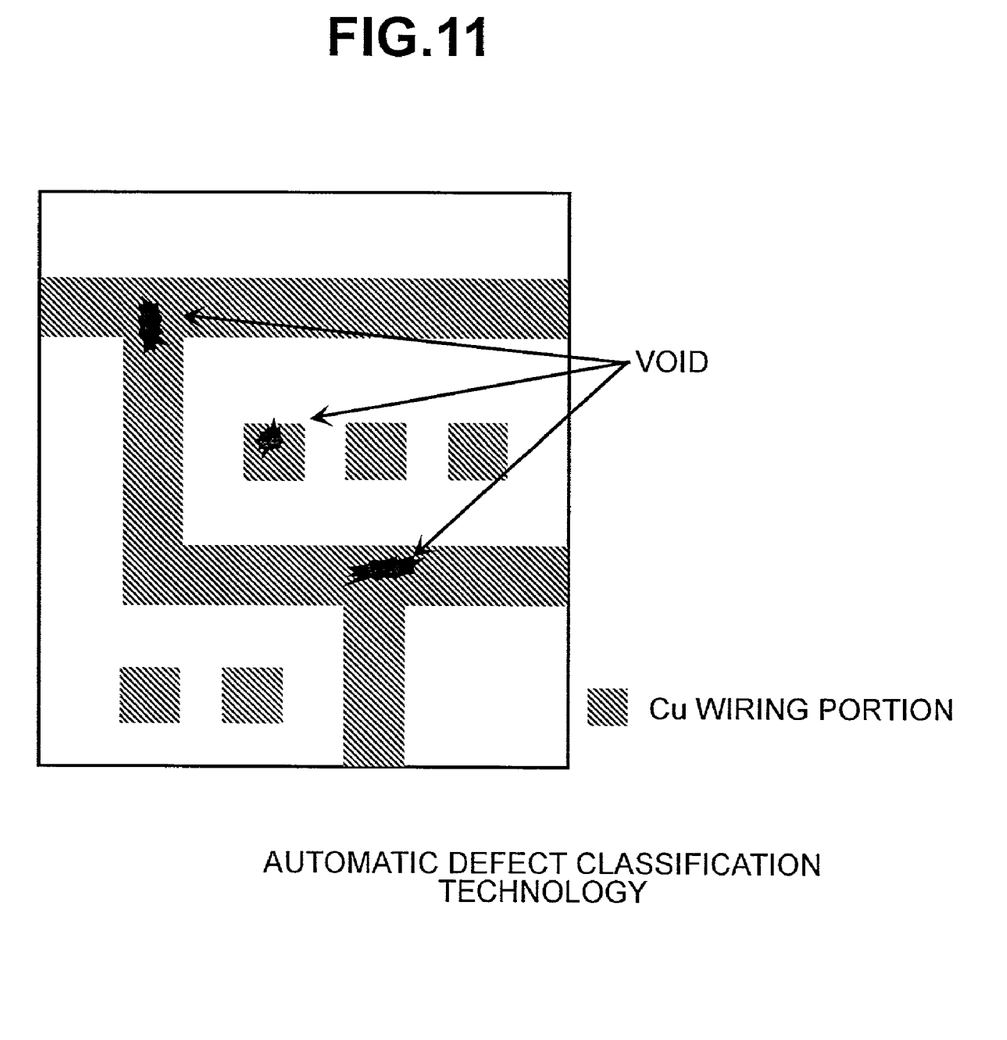
FIG. 11 is an enlarged plan view of a chip showing a defect on the chip.

FIG. 11 is an example that shows the pattern on which a defect exists by matching the coordinates of the detected defect and the design data. For example, voids have occurred in Cu wiring but there are no voids anywhere other than on that Cu wiring. Therefore, when automatically classifying defects, whether or not a defect exists in a particular amount in Cu wiring is useful information. This information can help to improve the precision of automatic defect classification. In a review using SEM, only defects on the surface can be reviewed because of SEM characteristics. By adding information concerning whether the defects are on the transparent film or the non-transparent film to the defect detection results, an efficient selection of defects that can be targeted by an SEM review is enabled.

Figure 12:
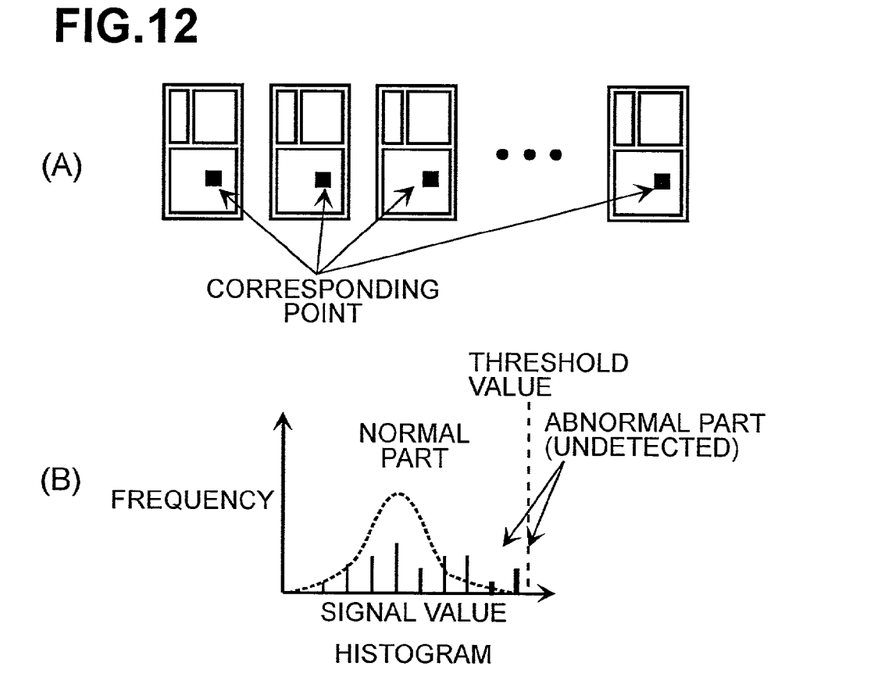
FIG. 12(a) is a plan view of a chip showing the corresponding point on the chip.
FIG. 12(b) is a histogram of signal values.
Figure 13:
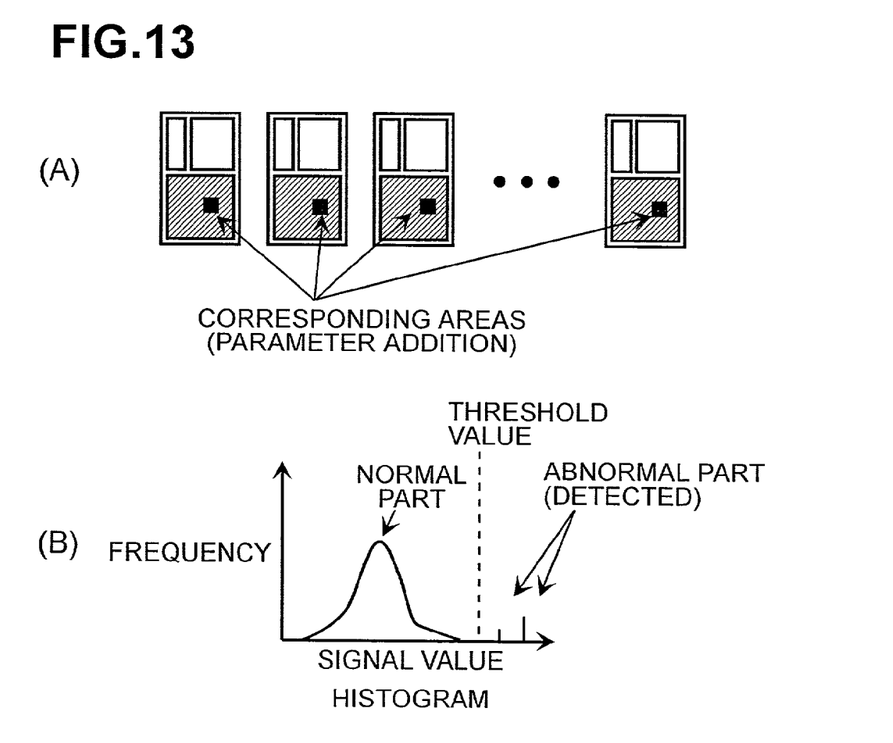
FIG. 13(a) is a plan view of a chip showing the corresponding point on the chip.
FIG. 13(b) is a histogram of signal values.

FIGS. 12 and 13 show examples in inspection devices that perform statistical processing in comparative inspection algorithms, in which stable conditions with few false alarms can be set by increasing the number of the statistical parameters using design data.

Statistical processing in comparative chip inspection postulates a signal value and frequency distribution using either signal from points that correspond to coordinates for each chip or signal differential values. A threshold value is set for the suggested distribution and anything exceeding this value is deemed to be an error. Here, if there are an insufficient number of chips on the wafer, there will be an insufficient number of parameters when statistics are collected and the reliability of the signal value frequency distribution will decrease. This will mean that false alarms will occur frequently. In this case, a higher threshold value is set and inspection conditions are set such that false alarms will not occur. This will mean that the overall sensitivity drops.

If design data is used, identical signals are obtained for identical patterns even for points other than those that correspond to coordinates for each chip and therefore, the number of parameters can be increased. The reliability of the suggested distribution increases with the increase in the number of parameters and the threshold value can be lowered. As a result, highly sensitive inspection with few false alarms is enabled.

Figure 14:
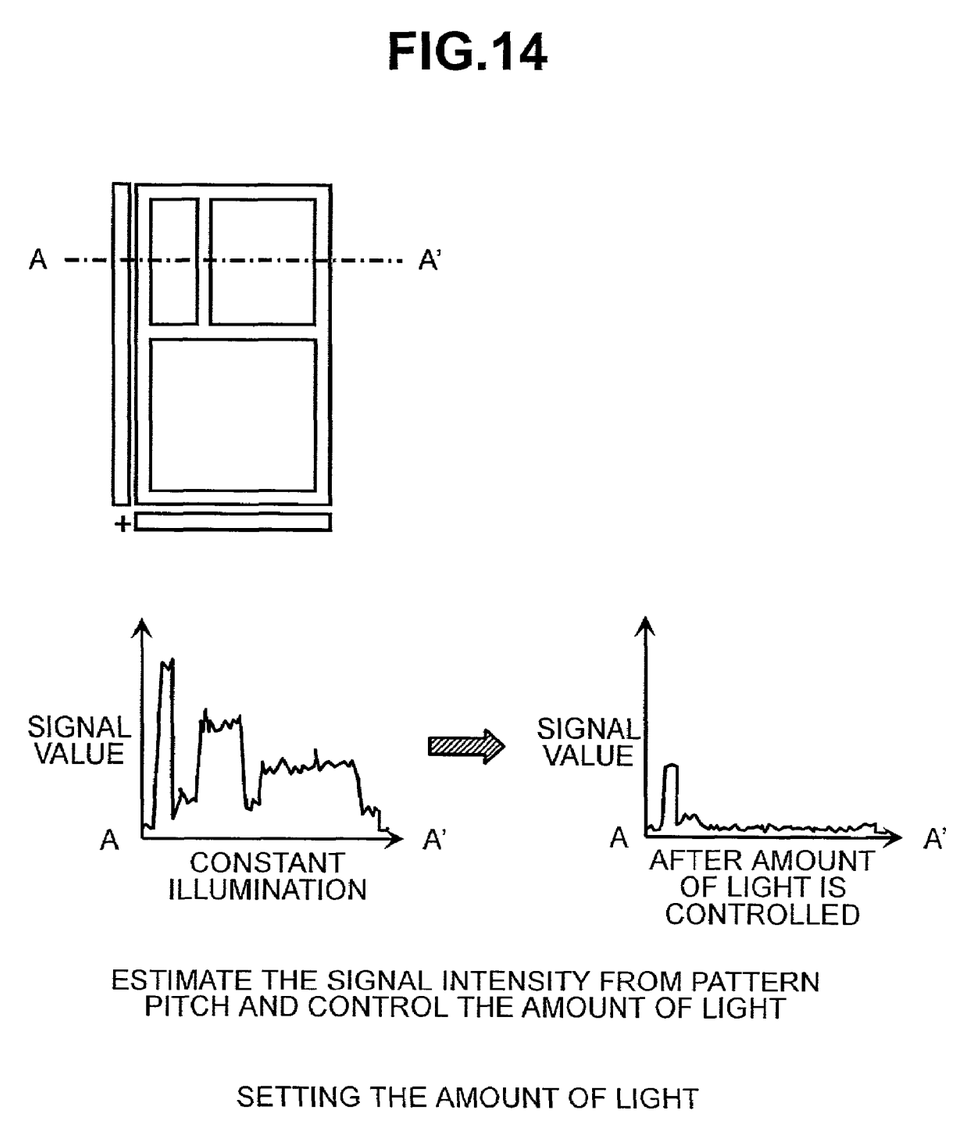
FIG. 14(a) is a plan view of a chip snowing the site of signal acquisition.
FIG. 14(b) is a graph showing the relationship between the amount of light and signal values.

FIG. 14 shows an example of a method in which the amount of light is controlled using the pattern density. The strength of light detected on entry into a sensor varies according to the pattern density and form. There is a dynamic range within the sensor and, for example, if a pattern does not shine very brightly the area cannot be inspected. Design data can be used to estimate, in advance, the amount of light that will be detected in each area. Control of the amount of light during inspection enables inspection of a broad area while maintaining sensitivity. The light control for each area can be automatically set based on the amount of light detected during the trial inspection.

Figure 15:
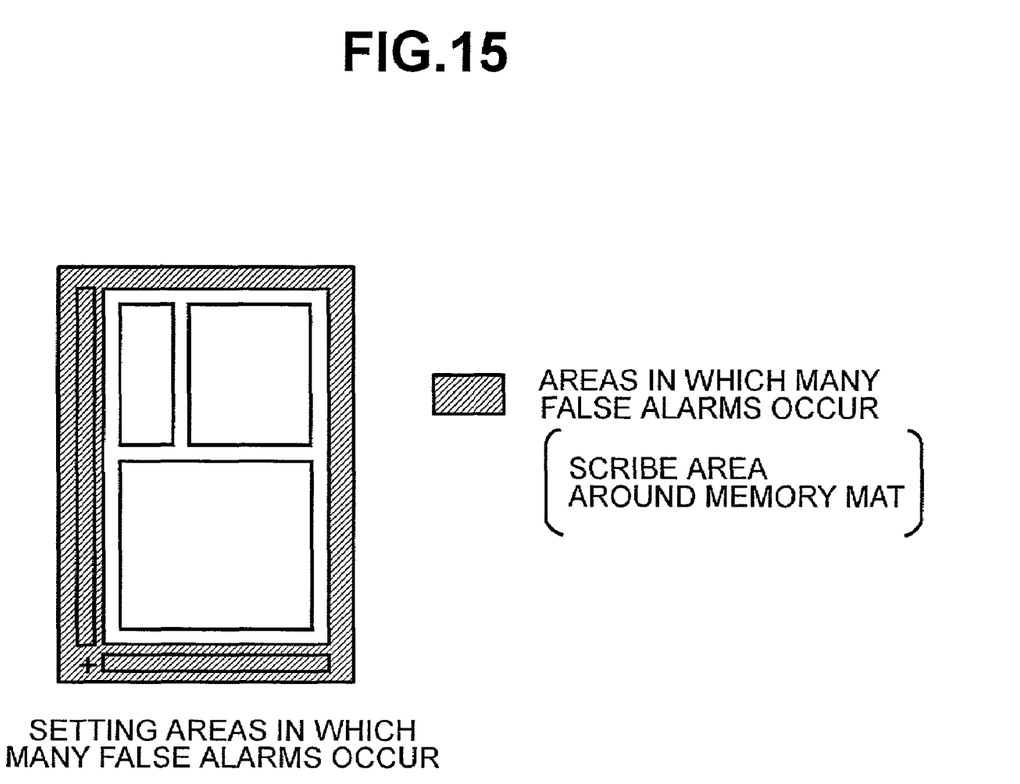
FIG. 15 is a plan view of a chip showing an area in which many false alarm occur.

FIG. 15 shows an area on a chip in which many false alarms occur. During the review that occurs after the trial inspection, areas in which many false alarms occur are isolated and reviewed. This enables the degree to which false alarms are occurring for temporary conditions to be judged in just a short time. This means that the time taken to tact conditions can be reduced.

As explained above, by using semiconductor device design data in the present invention: (1) the number of items that must be entered when setting conditions decreases and thus the time involved in setting conditions can be shortened; (2) the resultant reduction in the number of entry items means that the worker's load is decreased and the amount of training required for use of the inspection device is reduced; and (3) because inspection conditions can be temporarily set without using an actual wafer, the time during which wafers accumulate can be reduced.

The invention may be embodied in other specific forms without departing from the spirit of essential characteristics thereof. The present embodiment is therefore to be considered in all respects as illustrative and not restrictive, the scope of the invention being indicated by the appended claims rather than by the foregoing description and all changes which come within the meaning and range of equivalency of the claims are therefore intended to be embraced therein.

What is claimed is:

1. A method for inspecting semiconductor devices comprising:

receiving a product name of a semiconductor device to be inspected and a process name that identifies a process by which the semiconductor device is to be inspected;

accessing a design database to down load data required for preliminary preparation of inspection of the semiconductor device associated with the semiconductor device, wherein the data required for the preliminary preparation of the inspection of the semiconductor device is identified using the received product name and the received process name;

processing the down loaded data required for the preliminary preparation of the inspection of the semiconductor device to set temporary inspection conditions, wherein the temporary inspection conditions comprise at least one of an inspection area of the semiconductor device, an alignment pattern of the semiconductor device, a spacial filter associated with the semiconductor device, or an area of the semiconductor device to be excluded;

executing a trial inspection of the semiconductor device to detect defects;

classifying the detected defects according to whether the defect is on an optically transparent film;

revising the temporary inspection conditions using data obtained by the executed trial inspection; and inspecting another semiconductor device using the revised temporary inspection conditions, wherein the processing is performed before the semiconductor device to be inspected arrives at a location for the trial inspection and the temporary conditions are set without referencing the semiconductor device to be inspected.

2. The method for inspecting semiconductor devices according to claim 1, wherein one of the temporary inspection conditions identifies the inspection area of the semiconductor device as an area in which a false alarm is likely to occur.

3. A method for inspecting semiconductor devices comprising:

receiving a product name of a semiconductor device to be inspected and a process name that identifies a process by which the semiconductor device is to be inspected;

accessing a design database to down load data required for preliminary preparation of inspection of the semiconductor device associated with the semiconductor device, wherein the data required for the preliminary preparation of the inspection of the semiconductor device is identified using the received product name and the received process name;

processing the down loaded data required for the preliminary preparation of the inspection of the semiconductor device to set temporary inspection conditions, wherein the temporary inspection conditions comprise at least one of an inspection area of the semiconductor device, an alignment pattern of the semiconductor device, a special filter associated with the semiconductor device, or an area of the semiconductor device to be excluded;

executing a trial inspection of the semiconductor device to detect defects;

classifying the detected defects according to whether the defect is on an optically transparent film; and outputting results of the executed trial inspection, wherein the results include information on whether the detected defect is on an optically transparent film, wherein the processing is performed before the semiconductor device to be inspected arrives at a location for the trial inspection and the temporary conditions are set without referencing the semiconductor device to be inspected.

4. The method for inspecting semiconductor devices according to claim 3, wherein one of the temporary inspection conditions identifies the inspection area of the semiconductor device as an area in which a false alarm is likely to occur.

5. The method for inspecting semiconductor devices according to claim 3, further comprising revising the set temporary inspection conditions so that only actual foreign matter on the semiconductor device is detected as a defect or a false alarm is less than a preset amount.

6. A method for inspecting semiconductor devices comprising:

receiving a product name of a semiconductor device and a process name that identifies a process by which the semiconductor device is to be inspected;

accessing a design database to down load data required for preliminary preparation of inspection of the semiconductor device associated with the semiconductor device, wherein the data required for the preliminary preparation of the inspection of the semiconductor device is identified using the received product name and the received process name;

processing the down loaded data required for the preliminary preparation of the inspection of the semiconductor device to set temporary inspection conditions, wherein the temporary inspection conditions comprise at least one of an inspection area of the semiconductor device, an alignment pattern of the semiconductor device, a spacial filter associated with the semiconductor device, or an area of the semiconductor device to be excluded;

executing a trial inspection of the semiconductor device to detect defects;

classifying the detected defects according to whether the defect is on an optically transparent film; and outputting a result of the executed trial inspection, wherein the result identifies whether the detected defect can be reviewed by a scanning electron microscope, wherein the processing is performed before the semiconductor device to be inspected arrives at a location for the trial inspection and the temporary conditions are set without referencing the semiconductor device to be inspected.

7. The method for inspecting semiconductor devices according to claim 6, wherein images of the detected defects are displayed on a screen.

8. The method for inspecting semiconductor devices according to claim 6, further comprising revising the set temporary inspection conditions based on the classification of the detected defects.

9. A method for inspecting a semiconductor device comprising:

receiving a product name of a semiconductor device to be detected and a process name that identifies a process by which the semiconductor device is to be inspected;

accessing a design database to down load data required for preliminary preparation of inspection of the semiconductor device associated with the semiconductor device, wherein the data required for the preliminary preparation of the inspection of the semiconductor device is identified using the received product name and the received process name;

processing the down loaded data required for the preliminary preparation of the inspection of the semiconductor device to set temporary inspection conditions, wherein the temporary inspection conditions comprise at least one of an inspection area of the semiconductor device, an alignment pattern of the semiconductor device, a spacial filter associated with the semiconductor device, or an area of the semiconductor device to be excluded;

executing a trial inspection of the semiconductor device to detect defects; and classifying the detected defects according to whether the defect is on an optically transparent film, wherein the processing is performed before the semiconductor device to be inspected arrives at a location for the trial inspection and the temporary conditions are set without referencing the semiconductor device to be inspected.

10. The method of claim 9 further comprising revising the set temporary inspection conditions.

* * * * *